(12) United States Patent
McCormick et al.

(10) Patent No.: US 12,727,885 B2
(45) Date of Patent: Sep. 8, 2026

(54) METHOD AND DEVICE FOR TISSUE DEFECT CLOSURE

(71) Applicant: Davol Inc., Warwick, RI (US)

(72) Inventors: Daniel F. McCormick, Bolton, MA (US); Cuixiang Qu Spinney, North Attleboro, MA (US)

(73) Assignee: Davol Inc., Warwick, RI (US)

( * ) Notice: Subject to any disclaimer, the term of this patent is extended or adjusted under 35 U.S.C. 154(b) by 75 days.

(21) Appl. No.: 18/289,187

(22) PCT Filed: May 6, 2022

(86) PCT No.: PCT/US2022/028087
§ 371 (c)(1),
(2) Date: Nov. 1, 2023

(87) PCT Pub. No.: WO2022/236066
PCT Pub. Date: Nov. 10, 2022

(65) Prior Publication Data

US 2024/0215979 A1 Jul. 4, 2024

Related U.S. Application Data

(60) Provisional application No. 63/185,685, filed on May 7, 2021.

(51) Int. Cl.
*A61B 17/08* (2006.01)
*A61B 90/00* (2016.01)

(52) U.S. Cl.
CPC ........ *A61B 17/08* (2013.01); *A61B 2017/081* (2013.01); *A61B 2090/064* (2016.02)

(58) Field of Classification Search
None
See application file for complete search history.

(56) References Cited

U.S. PATENT DOCUMENTS 4,832,027 A * 5/1989 Utz ...................... A61B 17/083 606/215
4,924,866 A * 5/1990 Yoon ................... A61B 17/083 606/216

(Continued)

FOREIGN PATENT DOCUMENTS

CN 106 388 895 A 2/2017
CN 109348702 A 2/2019

(Continued)

OTHER PUBLICATIONS

Extended European Search Report mailed Feb. 10, 2025 for European Application No. 22799686.5.

(Continued)

*Primary Examiner* — Shaun L David
(74) *Attorney, Agent, or Firm* — Wolf, Greenfield & Sacks, P.C.

(57) ABSTRACT

Devices and methods for closure of apertures in tissue (e.g., defects in fascial tissue) are generally provided. Closure of apertures in tissue, e.g., using sutures and patch closures, are common surgical operations. In some aspects, methods and devices for using tissue grippers to engage tissue portions, and subsequently biasing the tissue grippers and tissue portions towards one another by changing a configuration of a lock are generally provided. In other aspects, methods and devices for measuring a retraction force applied by tissue grippers to tissue portions are generally provided.

27 Claims, 5 Drawing Sheets

(56) References Cited

U.S. PATENT DOCUMENTS 5,030,224 A * 7/1991 Wright ................ A61B 17/083 600/209
5,263,973 A * 11/1993 Cook .................... A61B 17/08 606/220
5,486,196 A * 1/1996 Hirshowitz ........... A61B 17/08 606/213
5,759,193 A * 6/1998 Burbank ............... A61B 17/08 606/151
5,893,879 A * 4/1999 Hirshowitz ........... A61B 17/08 606/217
6,273,903 B1 * 8/2001 Wilk ..................... A61B 17/10 606/151
6,471,715 B1 10/2002 Weiss
8,187,290 B2 5/2012 Buckman et al.
2011/0152738 A1 * 6/2011 Zepeda .................. A61L 15/26 602/53
2014/0088481 A1 3/2014 Jackson et al.
2014/0128819 A1 5/2014 Eaves
2014/0336701 A1 11/2014 McLorg
2015/0305847 A1 * 10/2015 Roll ..................... A61F 2/0045 600/30
2015/0327863 A1 11/2015 Smith et al.
2017/0319319 A1 * 11/2017 Fischer ............... A61B 17/068
2020/0323614 A1 10/2020 Lamps et al.

FOREIGN PATENT DOCUMENTS

CN 111700658 A 9/2020
EP 3 260 053 A1 12/2017
JP H08-150150 A 6/1996
JP H10-503387 A 3/1998
JP 2022-526076 A 5/2022
SU 1 412 751 A1 7/1988

OTHER PUBLICATIONS

International Search Report and Written Opinion mailed Sep. 22, 2022 for International Application No. PCT/US2022/028087.
International Preliminary Report on Patentability mailed Nov. 16, 2023 for International Application No. PCT/US2022/028087.

* cited by examiner

METHOD AND DEVICE FOR TISSUE DEFECT CLOSURE

CROSS-REFERENCE TO RELATED APPLICATIONS

This application is a national stage filing under 35 U.S.C. § 371 of International Patent Application Serial No. PCT/US2022/028087, filed May 6, 2022, which claims priority to U.S. Application Ser. No. 63/185,685, filed May 7, 2021, the disclosures of each of which are incorporated herein by reference in their entirety.

FIELD

Disclosed embodiments are related to methods and devices for tissue defect closure.

BACKGROUND

Closure of apertures in tissues, such as defects in fascial tissue, are common surgical operations. Such apertures may be formed during surgical operations, e.g., by the creation of an incision. In some cases, such apertures are naturally occurring as is the case with hernias. Sutures and patch closures are oftentimes used to close and repair apertures in tissue.

SUMMARY

In one aspect, a tissue closure device is provided. According to some embodiments, the tissue closure device comprises: a first tissue gripper; a second tissue gripper; a spring operatively coupled to the first tissue gripper and the second tissue gripper; and a lock configured to retain the first tissue gripper and the second tissue gripper in an extended configuration in a locked configuration, wherein the spring is configured to bias the first tissue gripper and the second tissue gripper towards a retracted configuration when the lock is in an unlocked configuration.

Another aspect is directed towards a method for closing an aperture in tissue. In some embodiments, the method comprises: retaining a first tissue gripper engaged with a first tissue portion and a second tissue gripper engaged with a second tissue portion in an extended configuration; changing a lock from a locked configuration to an unlocked configuration to release the first tissue gripper and the second tissue gripper from the extended configuration; and biasing the first tissue gripper towards the second tissue gripper to move the first tissue gripper and the first tissue portion towards the second tissue gripper and the second tissue portion.

In another aspect, a tissue closure device is provided. According to some embodiments, the tissue closure device comprises: a first tissue gripper; a second tissue gripper; a spring operatively coupled to the first tissue gripper and the second tissue gripper; a housing including a first housing portion and a second housing portion, wherein the first tissue gripper is operatively coupled to the first housing portion and the second gripper is operatively coupled to the second housing portion, wherein the spring is configured to bias the first tissue gripper and the second tissue gripper from an extended configuration towards a retracted configuration; and a force indicator configured to visually indicate a retraction force applied by the first and second tissue grippers to a first tissue portion and a second tissue portion.

In still another aspect, a method for closing an aperture in tissue is provided. In some embodiments, the method comprises: retaining a first tissue gripper engaged with a first tissue portion and a second tissue gripper engaged with a second tissue portion in an extended configuration; biasing the first tissue gripper towards the second tissue gripper to move the first tissue gripper and the first tissue portion towards the second tissue gripper and the second tissue portion; and visually indicating a retraction force applied by the first and second tissue grippers to the first and second tissue portions using a force indicator.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1A:
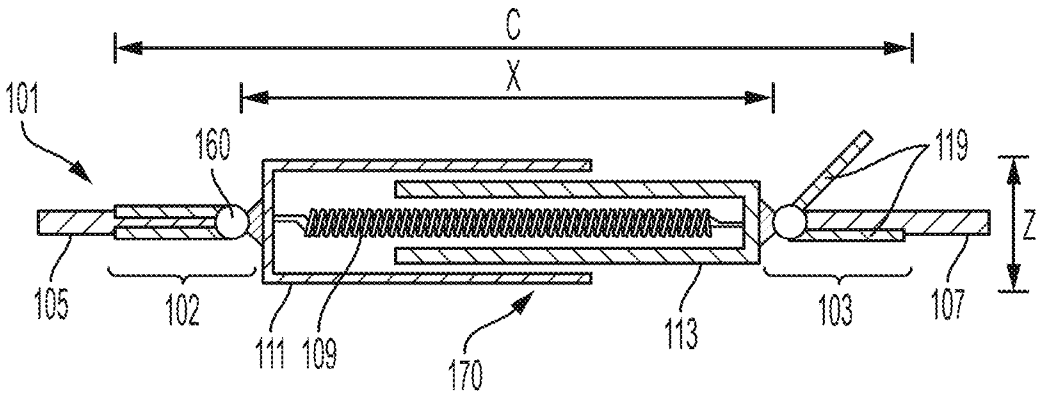
FIGS. 1A-1C present cross-sectional schematic illustrations of a device for tissue closure, according to certain embodiments.

Devices and methods for closure of apertures in tissue (e.g., defects in fascial tissue) are generally provided. Closure of apertures in tissue, e.g., using sutures and patch closures, are common surgical operations. However, in the context of the present disclosure, it has been recognized that improved methods and devices for atraumatically closing tissue apertures and determining forces required to fully close the apertures, and/or keep the apertures closed are needed. In some aspects, methods and devices for using tissue grippers to engage tissue portions, and subsequently biasing the tissue grippers and tissue portions towards one another to aid in closing an aperture formed in the tissue are generally provided.

The inventors have recognized that defects in fascial tissue, such as defects formed during herniation, or defects formed intentionally during other surgical operations can be difficult to close and repair without risking further damage to the fascial tissue. For example, sutures used to close fascial defects may tear through the fascial tissue as the sutures are tightened, causing the defect to reopen and suffer additional damage. The difficulty of repairing tissue in these cases may increase with the width of the fascial defect, where the width of a fascial defect, in some instances. Specifically, fascial defects with widths between or equal to 8 cm wide and 20 cm may be difficult to close using standard closure procedures.

The difficulty associated with fascial defect closure may also be compounded by the lack of visual indicators of tensile forces acting on the fascial tissue during typical procedures. For instance, many fascial tissue repairs are performed robotically. Due to the lack of tactile feedback, when performing such fascial tissue repairs, the main visual indicator of excessive stress on the fascial tissue is the tearing of sutures and/or tissue. Thus, the inventors have recognized it may be desirable to provide a visual indication of the tensile forces applied during the repair of the fascial defect.

In view of the above, the inventors have recognized the benefits associated with devices that can be attached to opposing portions of a fascial defect and transitioned between an extended configuration and retracted configuration to apply a force to help close the fascial defect. In addition to providing a tensile force to the fascial tissue surrounding a fascial defect, in some embodiments described herein, the device may also provide a visual indication of the forces applied to the tissue by the device.

In one embodiment, a tissue closure device may include a first tissue gripper configured to be engaged with a first issue portion and a second tissue gripper configured to be engaged with a second tissue portion, where the grippers may be maintained in a first extended configuration. In some embodiments, the device includes a lock that may transition from a locked configuration to an unlocked configuration to release the first tissue gripper and the second tissue gripper from the extended configuration. The first tissue gripper may be biased toward the second tissue gripper to move the first tissue gripper and the first tissue portion towards the second tissue gripper and the second tissue portion once the grippers are released from the extended configuration by the lock. In some embodiments, the inclusion of a lock may permit a user to attach the first and second tissue grippers to the tissue prior to applying a closing force to an aperture formed in the tissue.

In another aspect, a tissue closure device may be configured to indicate a force applied to the tissue. The device may include a first tissue gripper configured to be engaged with a first issue portion and a second tissue gripper configured to be engaged with a second tissue portion in a first extended configuration. The first tissue gripper may be biased toward the second tissue gripper to move the first tissue gripper and the first tissue portion towards the second tissue gripper and the second tissue portion. In some embodiments, the tissue closure device may include a force indicator that is configured to provide an indication of a retraction force applied by the first and second tissue grippers to the first and second tissue portions as described herein. Such measurements of the retraction force may help inform a surgeon of the force which may be needed to close the aperture. For example, this may aid the surgeon in deciding how best to close the aperture including the application of sutures, tissue patches, component separation, and/or additional devices for tissue closure.

Depending on the embodiment, the above-noted concepts of using a lock and/or force indicator may either be used individually and/or together. For example, in one embodiment, a device as described herein may be used, in some embodiments, to close an aperture in tissue. As a specific, non-limiting example, in certain embodiments, a device as described herein may be inserted into a tissue aperture (e.g., a fascial defect), locked into an extended configuration, so that a first tissue gripper can engage a first portion of tissue (e.g., fascial tissue). Next, the second tissue gripper is manipulated to engage with a second portion of tissue (e.g., fascial tissue), according to some embodiments. Following these steps, the device may be switched (e.g., using a robotic surgical system) from a locked configuration to an unlocked configuration. If the device can provide sufficient retraction force without slipping, the spring of the device in the unlocked configuration will bias the first tissue gripper towards the second tissue gripper to move the first tissue gripper and the first tissue portion towards the second tissue gripper and the second tissue portion. As needed, additional devices may be introduced, until the tissue aperture is sufficiently closed to allow surgical repair. In some embodiments, the need for additional devices may be indicated by a force indicator on the initial device, if the initial device is unable to fully retract on its own. Once the aperture has been closed, in some embodiments, the tissue may be sutured together, and the device or devices may be removed. Alternatively or in addition to suturing, a tissue patch may be used to close the aperture. In some embodiments, once a tissue aperture has been at least partially sutured or patched, the device for tissue closure may be disengaged from the tissue portions and/or removed from the tissue aperture.

As noted above, in some embodiments, a device may include a force indicator configured to visually indicate a retraction force applied by the first and second tissue grippers to a first tissue portion and a second tissue portion (e.g., which may be used to determine a retraction force applied by the first and second tissue grippers). Any appropriate type of force indicator may be used. For example, a force indicator, in some embodiments, includes a plurality of markings on an external surface of a first and/or second housing portion and a marker that is configured to move relative to the plurality of markings to indicate the applied force as the device transitions between an extended and retracted configuration to indicate the retraction force. Of course other types of force indicators including a force dial, digital reading display, and/or any other appropriate type of force indicator capable of visually indicating a force applied to the associated tissue may be used as the disclosure is not so limited.

According to certain embodiments, a device comprises a housing. The housing may include a first housing portion and a second housing portion. In some embodiments, the first tissue gripper is operatively coupled to the first housing portion and the second tissue gripper is operatively coupled to the second housing portion. A spring may be operatively coupled to the first housing portion and the second housing portion to bias the first housing portion towards the second housing portion. In some embodiments, at least a portion of the second housing portion is configured to slide into an interior volume of the first housing portion. In certain embodiments, the spring is at least partially disposed within an interior volume of the first housing portion and/or is at least partially within an interior volume of the second housing portion.

In some embodiments, a device may include a longitudinal axis (e.g., an axis extending along the direction of extension of a tissue closure device comprising the housing). According to certain embodiments, the device comprises a maximum longitudinal dimension (e.g., a length). Any suitable maximum longitudinal dimension may be used, depending on the desired application. However, according to certain embodiments, an advantageous maximum longitudinal dimension of the device in the extended configuration may approximately correspond to a maximum width of an aperture in tissue the device is intended to close (e.g., a fascial defect). Accordingly, in some embodiments, the device in the extended configuration may include a maximum longitudinal dimension of greater than or equal to 5 cm, greater than or equal to 8 cm, greater than or equal to 10 cm, greater than or equal to 12 cm, greater than or equal to 15 cm, or any other appropriate dimension. In some embodiments, in an extended configuration, the device comprises a maximum longitudinal dimension of less than or equal to 20 cm, less than or equal to 18 cm, less than or equal to 15 cm, less than or equal to 12 cm, less than or equal to 10 cm, less than or equal to 8 cm, or any other appropriate dimension. Combinations of these ranges are possible. For example, in some embodiments, in an extended configuration, the device may have a maximum longitudinal dimension of greater than or equal to 5 cm and less than or equal to 20 cm. Of course, maximum longitudinal dimensions in the extended configuration both greater than and less than those noted above are also contemplated as the disclosure is not so limited.

In a retracted configuration, in some embodiments, a device comprises a maximum longitudinal dimension of greater than or equal to 1 cm, greater than or equal to 1.2 cm, greater than or equal to 1.5 cm, greater than or equal to 2 cm, greater than or equal to 3 cm, greater than or equal to 5 cm, greater than or equal to 8 cm, or any other appropriate dimension. In a retracted configuration, in some embodiments, the device comprises a maximum longitudinal dimension of less than or equal to 10 cm, less than or equal to 8 cm, less than or equal to 5 cm, less than or equal to 3 cm, less than or equal to 2.5 cm, less than or equal to 2 cm, less than or equal to 1.5 cm, or any other appropriate dimension. Combinations of these ranges are possible. For example, in some embodiments, in a retracted configuration, the device comprises a maximum longitudinal dimension of greater than or equal to 1 cm and less than or equal to 10 cm. Of course, maximum longitudinal dimensions in the retracted configuration both greater than and less than those noted above are also contemplated as the disclosure is not so limited.

In some embodiments, a device may exhibit a longitudinal distance between a first tissue gripper of the device and a second tissue gripper of the device that may vary when the device transitions between an extended and a retracted configuration. In the extended configuration, in some embodiments, the longitudinal distance between the first tissue gripper and the second tissue gripper is greater than or equal to 1 cm, greater than or equal to 4 cm, greater than or equal to 6 cm, greater than or equal to 8 cm, greater than or equal to 10 cm, or any other appropriate dimension. In the extended configuration, in some embodiments, the longitudinal distance between the first tissue gripper and the second tissue gripper is less than or equal to 18 cm, less than or equal to 15 cm, less than or equal to 12 cm, less than or equal to 10 cm, greater than or equal to 8 cm, or any other appropriate dimension. Combinations of these ranges are possible. For example, in some embodiments, in the extended configuration, the longitudinal distance between the first tissue gripper and the second tissue gripper is greater than or equal to 1 cm and less than or equal to 18 cm. Of course, distances both greater than and less than those noted above are also contemplated.

In a retracted configuration, in some embodiments, the longitudinal distance between the first tissue gripper and the second tissue gripper of a device is greater than or equal to 0 cm, greater than or equal to 0.2 cm, greater than or equal to 0.5 cm, greater than or equal to 0.8 cm, greater than or equal to 1 cm, greater than or equal to 1.2 cm, greater than or equal to 1.5, or any other appropriate dimension. In the retracted configuration, in some embodiments, the longitudinal distance between the first tissue gripper and the second tissue gripper is less than or equal to 2 cm, less than or equal to 1.5 cm, less than or equal to 1.2 cm, less than or equal to 1 cm, greater than or equal to 0.8 cm, greater than or equal to 0.5 cm, or any other appropriate dimension. Combinations of these ranges are possible. For example, in some embodiments, in the retracted configuration, the longitudinal distance between the first tissue gripper and the second tissue gripper is greater than or equal to 0 cm and less than or equal to 2 cm. As a more specific example, in some embodiments, in the retracted configuration, the minimum distance between the first tissue gripper and the second tissue gripper is greater than or equal to 1 cm and less than or equal to 2 cm. Of course, ranges different from those noted above are also contemplated as the disclosure is not so limited.

According to certain embodiments, a device has a maximum transverse dimension, such as a width or diameter, which may be perpendicular to the maximum longitudinal dimension of the device. Any suitable maximum transverse dimension may be chosen. However, it may be advantageous, according to certain embodiments to choose a maximum transverse dimension that allows the device to be inserted through a surgical trocar. In some embodiments, the device has a maximum transverse dimension of greater than or equal to 3 mm, greater than or equal to 4 mm, greater than or equal to 5 mm, greater than or equal to 6 mm, greater than or equal to 7 mm, or any other appropriate dimension. In some embodiments, the housing has a maximum transverse dimension of less than or equal to 8 mm, less than or equal to 7 mm, less than or equal to 6 mm, less than or equal to 5 mm, less than or equal to 4 mm, or any other appropriate dimension. Combinations of these ranges are possible. For example, in some embodiments, the housing has a maximum transverse dimension of greater than or equal to 3 mm and less than or equal to 8 mm. In some embodiments, e.g., when the device does not need to be inserted through a surgical trocar, the device may have a maximum transverse dimension that is greater than or equal to 8 mm. Additionally, any other appropriate range of maximum transverse dimensions both greater than and less than those noted above may also be used as the disclosure is not so limited.

Various embodiments disclosed herein may use a spring. In these embodiments, it should be understood that any appropriate spring capable of applying a force to bias the tissue grippers of a device towards one another may be used. In some embodiments, it may be advantageous to use an extension spring. According to certain embodiments, the spring is a coil spring (e.g., a spring comprising a coil of material, such as metal), configured to act as an extension spring. For example, the spring may be operatively connected to the first tissue gripper and the separate tissue gripper, such that increasing a distance between the first tissue gripper and the second tissue gripper causes extension of the spring. According to certain embodiments, the spring is a coil spring (e.g., a spring comprising a coil of material, such as metal), configured to act as a compression spring. For example, the spring may be disposed between a first portion of the housing and a second portion of a housing, such that as the first housing portion slides away from the second housing portion, the coil spring is compressed between the two housing portions. The spring may also be an elastic component, such as an elastic band, an elastic tube, and/or any other elastic structure capable of being used as a spring (e.g, comprising a polymeric material that, under an applied load, may be elastically deformed by greater than or equal to 20%, greater than or equal to 30%, greater than or equal to 50%, greater than or equal to 100%, or more of its undeformed length). Other appropriate types of springs may include, but are not limited to, a drawbar spring, gas spring, torsion spring, rotary spring, and/or any other appropriate type of spring as the disclosure is not so limited.

According to certain embodiments, it may be advantageous for a spring to be approximately linearly elastic. Generally, a change in force applied to a linearly elastic spring will result in a proportional change in length of the linearly elastic spring. According to certain embodiments, this may be advantageous for determining a retraction force applied by a first tissue gripper and a second tissue gripper operatively couple to the spring, because the retraction force is proportional to the displacement, allowing the retraction force to be determined using regularly spaced markers to indicate displacement. However, linearly elastic springs are not a requirement, and in some embodiments, irregularly spaced markers or other methods may be used to indicate a retraction force, as described in more detail below.

Turning now to the tissue grippers, in some embodiments, a tissue gripper is configured to engage with a tissue portion (e.g., in order to apply a retraction force to the tissue portion). Generally, a tissue gripper may have any appropriate dimensions. However, in order to reduce a potential for damage to the tissue portion, it may be advantageous for the tissue gripper to distribute a force (e.g., a retraction force) over a relatively wide area. For example, according to certain embodiments, a tissue gripper has a length that may extend in a direction that is parallel to a longitudinal axis of the gripper and/or overall device. Additionally, the gripper length may extend in a direction that is configured to be perpendicular to an edge of a portion of tissue engaged by the gripper. In some embodiments, the tissue gripper has a length of greater than or equal to 1 cm, greater than or equal to 1.2 cm, greater than or equal to 1.4 cm, greater than or equal to 1.6 cm, greater than or equal to 1.8 cm, or any other appropriate dimension. In some embodiments, the tissue gripper has a length of less than or equal to 2 cm, less than or equal to 1.8 cm, less than or equal to 1.6 cm, less than or equal to 1.4 cm, less than or equal to 1.2 cm, or any other appropriate dimension. Combinations of these ranges are possible. For example, in some embodiments, tissue gripper has a length of greater than or equal to 1 cm and less than or equal to 2 cm though ranges both greater and less than these are also contemplated as the disclosure is not so limited.

In some embodiments, a tissue gripper has a width that may extend in a direction that is transverse to a longitudinal axis of the gripper and/or overall device. Additionally, the gripper width may extend in a direction that is configured to be parallel to an edge of a portion of tissue engaged by the gripper. A tissue gripper may have any suitable width. However, as mentioned above, it may be advantageous to choose a width that allows the device to be inserted through a surgical trocar. In some embodiments, the tissue gripper has a width of greater than or equal to 3 mm, greater than or equal to 4 mm, greater than or equal to 5 mm, greater than or equal to 6 mm, greater than or equal to 7 mm, or greater. In some embodiments, the tissue gripper has a width of less than or equal 8 mm, less than or equal to 7 mm, less than or equal to 6 mm, less than or equal to 5 mm, less than or equal to 4 mm, or less. Combinations of these ranges are possible. For example, in some embodiments, the tissue gripper has a width of greater than or equal to 3 mm and less than or equal to 8 mm. In some embodiments, e.g., when the device does not need to be inserted through a surgical trocar, or through the use of flexible or foldable tissue grippers, the tissue gripper may have a width exceeding 8 mm as the disclosure is not thus limited.

According to some embodiments, a tissue gripper is configured to apply a combination of forces to the tissue portion with which it engages. In some applications, these forces may include a first force component corresponding to a compressive force applied to the tissue disposed between opposing jaws of a gripper as well as a second force component which may correspond to a shear force applied to the tissue when drawing opposing portions of a tissue aperture towards one another. In some instances, this shear force may also be referred to as a retention force that retains the tissue in the tissue gripper when a tensile force is applied to the gripper.

In some embodiments, a clamping force applied to tissue by a tissue gripper engaged with the tissue may be applied uniformly across the area of the gripper. However, embodiments in which non-uniform distributions of force are applied to tissue by a tissue gripper are also contemplated. According to certain embodiments, a total clamping force applied by a gripper to engaged tissue is greater than or equal to 0.5 N, greater than or equal to 1 N, greater than or equal to 1.5 N, greater than or equal to 2 N, greater than or equal to 3 N, greater than or equal to 5 N, greater than or equal to 8 N, greater than or equal to 10 N, greater than or equal to 15 N, or any other appropriate clamping force. In some embodiments, the total clamping force is less than or equal to 20 N, less than or equal to 15 N, less than or equal to 10 N, less than or equal to 8 N, less than or equal to 5 N, less than or equal to 3 N, less than or equal to 2 N, less than or equal to 1.5 N, or less, or any other appropriate clamping force. Combinations of these ranges are possible. For example, in some embodiments, the total clamping force is greater than or equal to 0.5 N and less than or equal to 20 N. In some instances the clamping forces applied by a tissue gripper may be measured using a load cell and/or may be calculated based on the known design parameters of the gripper.

In some embodiments, a tissue gripper may be configured to apply a maximum retention force to tissue held within the tissue gripper prior to the tissue slipping within the grippers. In some embodiments, the maximum retention force of the tissue gripper is designed to accommodate the maximum break force of the existing absorbable sutures. The maximum retention force may be greater than or equal to 2.5 N, greater than or equal to 3 N, greater than or equal to 3.5 N, greater than or equal to 4 N, greater than or equal to 4.5 N, greater than or equal to 5 N, or any other appropriate retention force. In some embodiments, the maximum retention force of the tissue gripper is less than or equal to 6 N, less than or equal to 5.5 N, less than or equal to 5 N, less than or equal to 4.5 N, less than or equal to 4 N, less than or equal to 3.5 N, or any other appropriate retention force. Combinations of these ranges are possible. For example, in some embodiments, the maximum retention force of the tissue gripper is greater than or equal to 2.5 N and less than or equal to 6 N. The maximum retention force of the tissue gripper may be measured, according to certain embodiments, by measuring a maximum shear force that can be applied in a tensile tester when the gripper is engaged with tissue analogous to human tissue (e.g., fascial tissue collected from a pig with an appropriate thickness to be gripped in the tissue grippers for testing).

In some embodiments, where a tissue gripper is configured to apply a retraction force to an engaged tissue portion, the retraction force applied by the tissue gripper to opposing tissue portions of a tissue aperture may be equal to the retention force the tissue gripper applies to the engaged tissue. Thus, the above noted maximum retention forces may also correspond to maximum retraction forces that may be applied by a given tissue gripper in some embodiments. Of course, retraction and/or retention forces that are greater than or less than those noted above are also contemplated as the disclosure is not so limited.

Any appropriate type of tissue gripper capable of transitioning between a closed configuration to engage with tissue and an open configuration to release the tissue may be used with the various embodiments described herein. For example, in some embodiments a tissue gripper may be single action (e.g., may transition between the open configuration and the closed configuration via the motion of a single jaw, relative to the device). The tissue gripper may also be double action (e.g., may transition between the open configuration and the closed configuration via the motion of two jaws, relative to the device). The tissue gripper may be fenestrated (e.g., may incorporate an open area or window into one or both jaws to offer a safer grip). The tissue gripper may be unfenestrated (e.g., may comprise solid jaws, relying on friction to hold the tissue). Additionally, in some embodiments, the first tissue gripper and/or the second tissue gripper may be biased towards the closed configuration. For example, a tissue gripper may comprise a spring clip, which may be biased by a spring such as a torsion spring (e.g., a rotary spring), a compression spring (e.g., a coil spring configured to operate under compression) or an expansion spring as described above. However, in other embodiments, the first tissue gripper and/or the second tissue gripper are biased towards the open configuration. As one, nonlimiting example, in some embodiments, an over-tube is configured to close a tissue gripper biased towards the open configuration when the over-tube is slid towards an end of the tissue gripper causing the jaws of the gripper to be closed. In view of the above, it should be understood that these embodiments are nonlimiting, and that any method and/or construction for providing a tissue gripper capable of releasably engaging tissue may be used as the disclosure is not limited in this fashion.

In some embodiments, it may be desirable to avoid damaging tissue engaged by a tissue gripper. Accordingly, a tissue gripper (e.g., a first tissue gripper, a second tissue gripper) may be configured to apply force to a tissue portion atraumatically (e.g., without puncturing, tearing, crushing, or otherwise damaging the tissue portion), in certain embodiments. Generally, the atraumatic application of force may be provided in a variety of ways. For example, a first tissue engaging surface and/or a second tissue engaging surface of the tissue gripper may comprise one or more types of textured feature, such as ridges, bumps, grooves, and/or teeth that are configured to provide frictional engagement with the tissue without damaging the tissue. In some embodiments, the inclusion of textured features on tissue engaging surfaces of the tissue gripper may increase the maximum retention force of the tissue gripper without risking additional traumatic damage to the engaged tissue portion. In some embodiments, the tissue grippers of a device may be configured to release an associated engaged tissue portion atraumatically, if the retraction force would otherwise exceed a threshold value. In some embodiments, this threshold force may be less than a maximum retention force of a tissue gripper static friction as described above, resulting in the release of the tissue portion. An advantage of such embodiments is that they reduce the risk of tissue damage in cases where a retraction force applied to tissue might otherwise result in slipping of the tissue within the tissue grippers.

According to certain embodiments, the device further comprises a lock configured such that when the lock is in a locked configuration, the device is retained in an extended configuration. In a locked configuration, the first tissue gripper and the second tissue gripper are held at a fixed distance from one another, whereas in an unlocked configuration the first tissue gripper and the second tissue gripper may move relative to one another, in response to external forces and biasing forces applied to the tissue grippers from a spring or other structure. The inclusion of a lock may be advantageous for a number of reasons. For example, a lock may be used to maintain an extended configuration of the device prior to engagement of tissue grippers of the device with tissue portions, reducing the need for extraneous manipulations of the device and/or tissue prior to unlocking of the device.

Any suitable locking mechanism may be used. For example, in some embodiments, the lock is a slot and key lock, which comprises a slot, located on a first portion of a housing of the device, and a key, located on a second portion of a housing of the device. In some such embodiments, the device may be locked or unlocked via a rotational motion of one housing portion relative to the other such that the key may slide into or out of a correspondingly sized and shaped slot configured to receive and retain the key in the locked configuration. In some embodiments, the lock is a spring detent, configured such that in the locked configuration, a spring traps a ball, or other correspondingly sized and shaped structure, against a hole, indentation, or other type of detent to lock the device in a desired configuration. In some embodiments, the lock is a cantilever lock, e.g., wherein a second housing portion comprises a cantilever connected to a key, and wherein a first housing portion comprises a catch such as a hole, indentation, or other structure configured to receive the key. In some such embodiments, depressing the key elastically deforms the cantilever, releasing the key from the catch to allow the first housing portion to slide relative to the second housing portion. In such embodiments, the second housing portion may include multiple catches, detents or keyway features to enable the first housing portion to be indexed unilaterally to a specified extended length prior to use to accommodate varying defect sizes. Other locking mechanisms are possible, and the disclosure is not thus limited. For certain applications, including surgeries performed using robotic surgical systems, pushbutton locks such as cantilever locks and/or slot and key locks may be advantageous, because they can be more easily manipulated by the robotic surgical system.

In some embodiments, devices described herein may be non-toxic and sterile before use. The device may comprise any appropriate materials. For example, the device described herein may comprise any appropriate combination of biocompatible metals, polymers, ceramics, combinations of the forgoing, and/or any other appropriate type of material. In some embodiments, the device is configured for reuse. However, in some embodiments, the device is intended to be disposable, and single use.

In some embodiments, materials used to construct the devices described herein may be capable of being easily sterilized. A variety of techniques exist for sterilizing materials, including UV irradiation, ethylene oxide (ETO) sterilization, gamma irradiation, autoclaving, or sterilizing using dry heat. In some embodiments, polymeric materials are chosen, because these are easier to sterilize for one time use (e.g., using ETO or gamma irradiation). However, in some embodiments, metals may be chosen, because they are more easily sterilized for multiple use. For example, in some embodiments, metals are autoclaveable, and are less prone to degradation during autoclaving and/or sterilizing using dry heat.

In some embodiments, materials may be chosen instead for their mechanical properties. For example, in some embodiments, metal may be a preferred material for the spring, because metal springs may be less prone to fracture than polymeric springs, or because metal springs may have more linearly elastic behavior than polymeric springs. However, in other embodiments, a polymer may be preferred for the spring (e.g., an elastic band) because it is less expensive or as a preferred elastic deformation profile. Similar advantages and disadvantages for each material exist for each component describe herein. Therefore, depending on the application, in some embodiments a device may comprise both plastic and metal components, and the disclosure is not thus limited.

Devices and methods as described herein may be used to close any type of aperture in tissue. For example, the aperture may be a defect in fascial tissue, in some embodiments. Such a fascial defect may occur naturally, e.g., due to the formation of a hernia. Tissue apertures, and apertures in fascial tissue may also form as a result of an incision made during a surgical procedure, and particularly in the case of large incisions, closing these apertures may be challenging by ordinary methods. Fascial defects may also occur as a result of traumatic injury. Applications and methods described herein may be used to close tissue apertures (e.g., fascial defects) regardless of origin, and the disclosure is not thus limited.

In some embodiments, devices and methods described herein may be used for laparoscopic surgeries. In some such embodiments, devices may be inserted into a patient via a trocar inserted into an incision smaller 2 cm in diameter. In certain embodiments, devices and methods described herein may be performed using robotic surgical systems. For example, the devices and methods herein may be performed laparoscopically using a robotic surgical system. The robotic surgical system may comprise components configured to operate a lock of a device, and/or to provide visual feedback to an operator of the robotic surgical system, according to certain embodiments. In some embodiments, the robotic surgical system may be used to engage or disengage tissue grippers from tissue portions. In certain embodiments, locks and tissue grippers described herein may be selected to be operable by a robotic surgical system.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

Figure 1B:
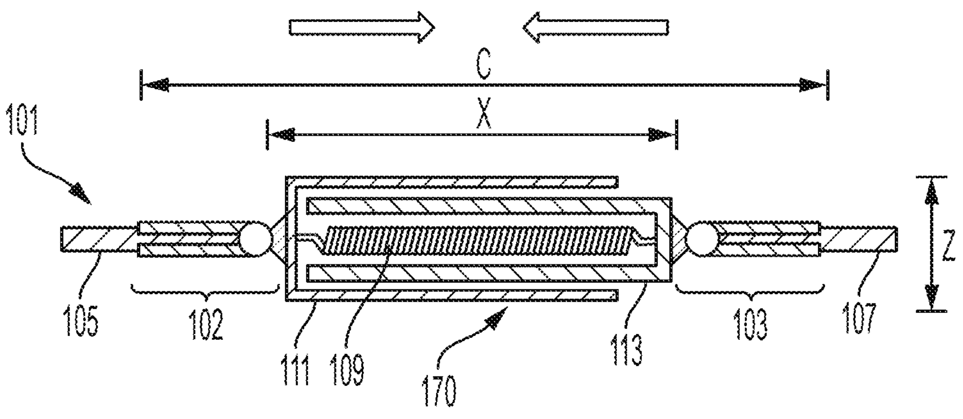
Figure 1C:
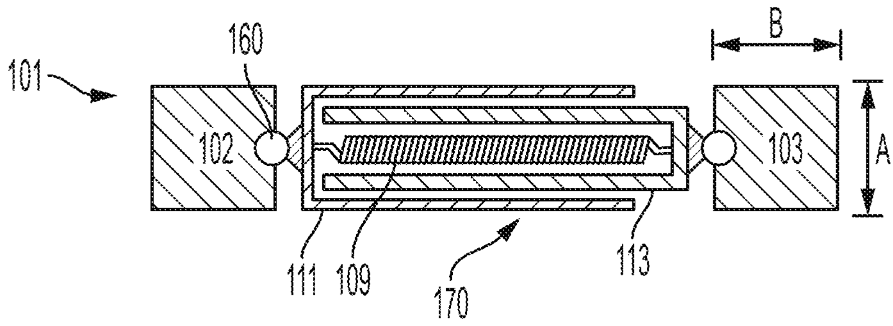

FIGS. 1A-1C present an exemplary embodiment of a tissue closure device, according to certain embodiments. As in FIG. 1A, a tissue closure device 101 may comprise a first tissue gripper 102 and a second tissue gripper 103. Each tissue gripper may comprise two opposing jaws with two tissue engaging surfaces 119 that are oriented towards one another. In FIG. 1A, the first tissue gripper 102 is engaged with a first tissue portion 105, with one tissue engaging surface pressed against each side of the first tissue portion 105 such that the first tissue portion is compressed between the opposing tissue engaging surfaces of the opposing jaws of the first tissue gripper. The second tissue gripper 103 is depicted in the open configuration such that it is not engaged with a second tissue portion 107, since only one of tissue engaging surfaces 119 is pressed against the second tissue portion 107. The second tissue gripper is depicted in the closed configuration in FIG. 1B. Each tissue engaging surface may comprise one or more types of textured feature, such as ridges, bumps, grooves, and/or teeth (not shown). The tissue grippers each may comprise a hinge 160, or other connecting structure, that movably connect the jaws of the associated gripper to one another and allow the tissue grippers to transition between the open and closed configurations. In some embodiments, the hinge 160 is associated with a torsional spring (not shown), in some embodiments, that is configured to bias the jaws of an associated tissue gripper to the closed configuration. However, other types of tissue grippers may also be used as elaborated on above.

Each of the tissue grippers 102 and 103 may be connected to a housing 170 of a device in some embodiments using any appropriate type of connection. In the depicted embodiment, hinges 160 connect the jaws the tissue grippers to the housing an associated portion of the housing. However, other types of connections may also be used as the disclosure is not so limited. In the depicted embodiment, the housing comprises a first housing portion 111 and a second housing portion 113. In some embodiments, such as those depicted in FIGS. 1A-1C, the first housing portion 111 and the second housing portion 113, are coaxially aligned tubes with open ends oriented towards one another. The tubes are sized and shaped such that the open ends allow the second housing portion 113 to slide at least partially into an interior volume of the first housing portion 111. However, the first and second housing portions may have any appropriate shape and/or overall construction such that the housing portions may move relative to one another to transition between an extended and retracted configuration.

As illustrated in the figures, in some embodiments, the second housing portion 113 is configured such that at least a portion of the second housing portion 113 can slide within the first housing portion 111. A spring 109 is disposed within the housing 170 and is illustrated in an extended configuration, in the example of FIG. 1A. The spring 109 is connected to the first housing portion 111 and the second housing portion 113 such that the device 101 is biased towards a closed configuration, in some embodiments. The spring 109 may be coaxial with the housing 170 as shown in FIGS. 1A-1C, though instances in which the spring is not coaxial with the associated housing portions are also contemplated. As shown in the figures, in some embodiments, the spring 109 is at least partially disposed within an interior volume of the first housing portion 111 and/or is at least partially within an interior volume of the second housing portion 113. As shown in FIG. 1A, the device 101 may have a maximum longitudinal dimension, or length, C, in the extended configuration, as described elsewhere, herein. The device 101 may also have a maximum transverse dimension, or width, Z, and a minimum distance between tissue grippers, X, as described elsewhere, herein.

The spring 109 may be connected to the housing 170 by any appropriate method. For example, the spring may be operatively coupled a device portion, such as the first tissue gripper 102, the second tissue gripper 103, the first housing portion 111, and/or the second housing portion 113, using mechanical fixtures, pins, hooks, loops, mechanically interlocking parts, welds, adhesives, combinations of the foregoing, and/or any other appropriate type of connection. While several nonlimiting types of connections are described above for connecting a spring to an associated portion of a housing, it should be understood that any appropriate type of construction and/or method for connecting a spring to a portion of the housing may be used as the disclosure is not thus limited.

FIG. 1B presents the device of FIG. 1A in a retracted configuration. Here, the second tissue gripper has been closed to engage the second tissue portion 107. The device has also been released such that the spring 109 applies a force that biases the housing portions, and associated tissue grippers, towards one another. Correspondingly, a retraction force is applied to the first tissue portion 105 and the second tissue portion 107 such that these opposing tissue portions are drawn towards one another as the device transitions from the initial extended configuration towards a retracted configuration. As the first housing portion 111 and the second housing portion 113 are displaced in words, the tension applied by the spring 109 biasing the housing portions towards one another is reduced, and the portion of the second housing portion 113 disposed within the interior of the first housing portion 111 is increased, according to certain embodiments. FIG. 1C presents the device of FIG. 1A, rotated 90 degrees around the longitudinal axis of the device, so that the width, A, and the length, B, of the jaws of the tissue grippers may be seen.

Figure 2A:
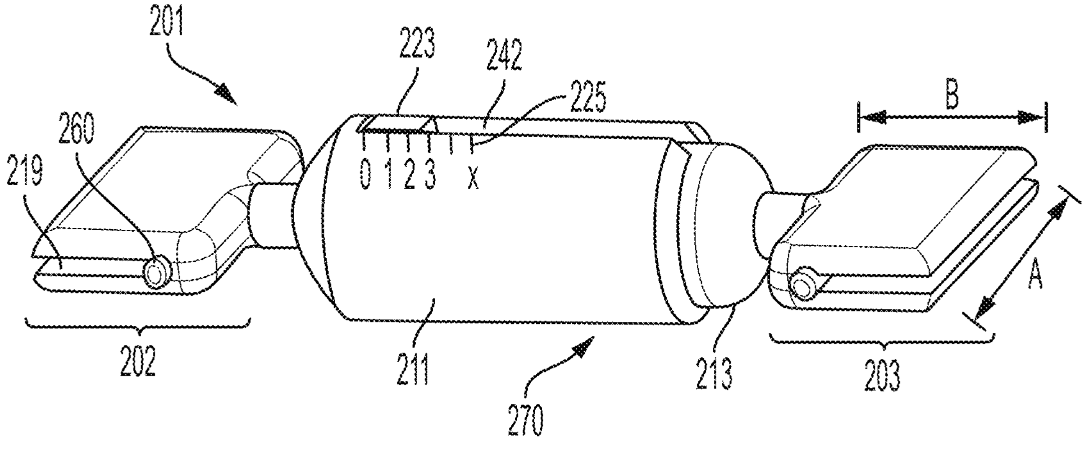
FIGS. 2A-2B present perspective illustrations of a device for tissue closure, according to certain embodiments.
Figure 2B:
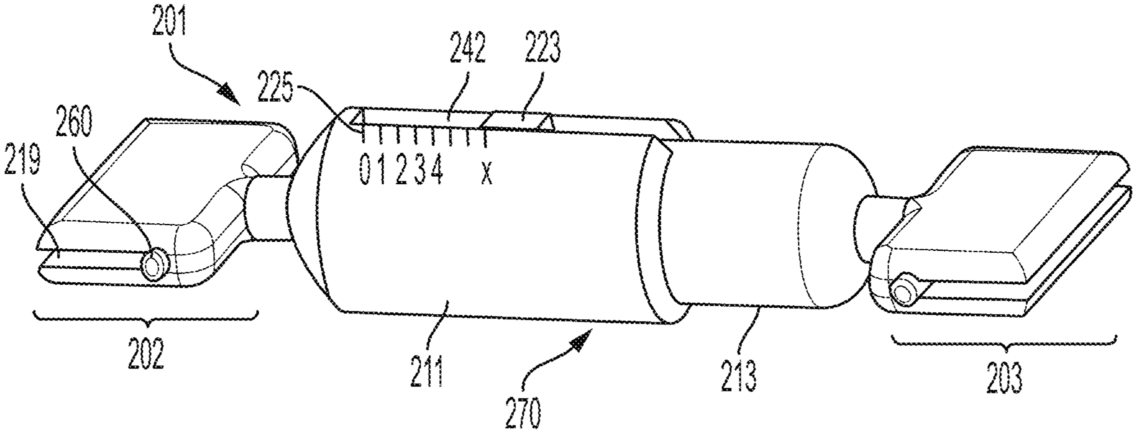

Turning now to FIGS. 2A-2B, an embodiment of a tissue closure device 201 is presented. The tissue closure device 201, in the exemplary embodiment of FIG. 2A, is shown in a retracted configuration, and comprises first and second tissue grippers 202 and 203, comprising a hinge 260 and tissue engaging surfaces 219 formed on two opposing jaws of the tissue gripper. In embodiments such as those of FIGS. 2A-2B, the first and second tissue grippers are connected to corresponding first and second housing portions 211 and 213 of a housing 270 of the tissue closure device 201. Similar to the embodiment of FIGS. 1A-1C, the first housing portion 211 may include an interior volume that is sized and shaped to receive at least a portion of the second housing portion 213.

As noted above, in some embodiments, a device may include a force indicator configured to visually indicate a retraction force applied by the first tissue gripper 202 and the second tissue gripper 203 to a first tissue portion and a second tissue portion (not shown). In the depicted embodiment, a groove 242 is formed in and extends at least partially along a length of the first housing portion. Correspondingly, a marker 223 may be operatively coupled to the second housing portion and aligned with and/or positioned with the groove. A plurality of markings 225, such as force readings, may be provided, i.e., printed, engraved, or otherwise formed, on the first housing portion 211. In some embodiments, the plurality of markings 225 are regularly spaced, and may be used to determine a displacement of the marker from the retracted configuration, though irregularly spaced markings may also be used. As the housing portions move relative to one another, the marker 223 connected to the second housing portion 213 is configured to move within the associated groove formed in the first housing portion relative to the plurality of markings. Thus, as the device transitions between the extended and retracted configurations the marker may be aligned with different markings to indicate the applied retraction force. In this embodiment, the marker 223 is depicted as a rectangular prism connected to a portion of a housing. However, in general, any appropriate type of marking may be used including, for example: differently shaped protrusions; indicator markings that are printed on or formed in a portion of the housing; labels applied to the housing; and/or any other appropriate feature applied, connected, or otherwise associated with a portion of the device housing that may be used to indicate a force applied to the tissue.

FIG. 2B shows the device 201 of FIG. 2A in the extended configuration. Whereas in FIG. 2A, marker 223 corresponds to the 0 marking 225, indicating that the device is fully retracted, in FIG. 2B, marker 223 corresponds to a position of a final marking 225, indicating that the device 201 is in the extended configuration. For configurations in between, the relative position of the marker 225 and the plurality of markings 225 may be used to visually indicate a force currently applied to the tissue by the device 201.

Figure 3:
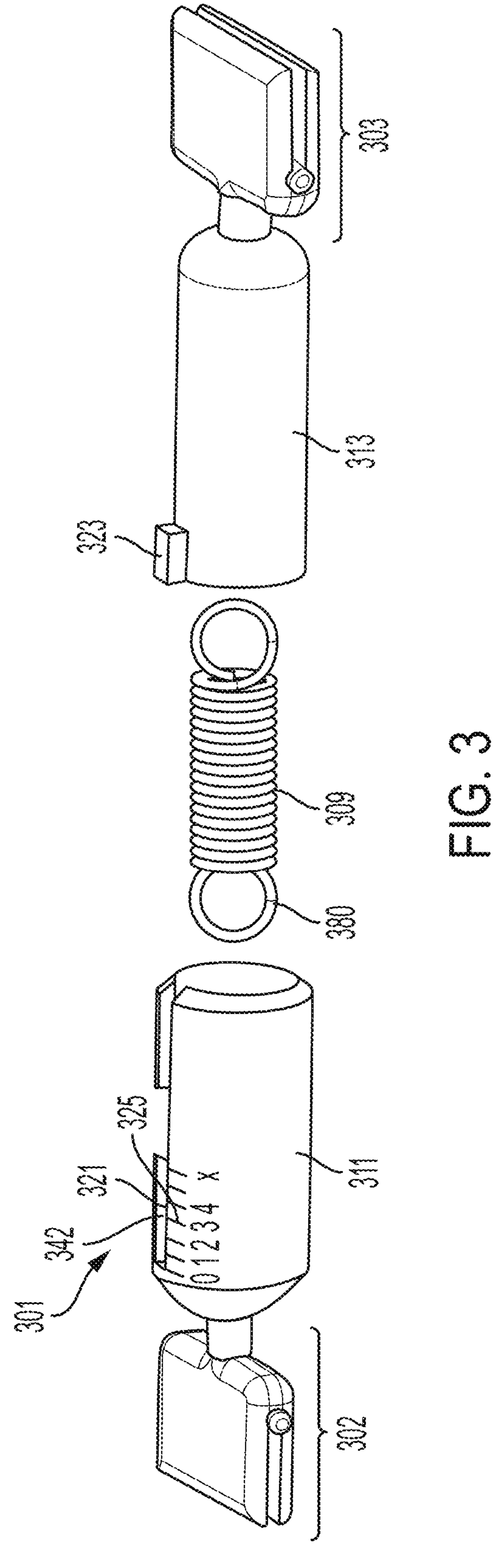
FIG. 3 presents an exploded perspective illustration of a device for tissue closure comprising a lock, according to certain embodiments.

FIG. 3 shows an exploded perspective illustration of another tissue closure device 301 according to one embodiment. Similar to the above embodiments, the tissue closure device 301 comprises a first tissue gripper 302 and a second tissue gripper 303 connected to first and second housing portions 311 and 313. The housing portions may again be formed as tubes with at least one open end, though other constructions may also be used. A groove 342 may be formed in and extend along at least a portion of a length of the first housing portion. The groove may include a first lock portion 321 that is positioned along a length of the groove. In the depicted embodiment, the first lock portion corresponds toa slot formed at a predetermined position along the length of the groove. A corresponding second lock portion 323 may be coupled to the second housing portion. In some embodiments, the second lock portion is a key, such as the depicted protrusion which may be sized and shaped such that it may be positioned within and slide along the groove. The key may also be sized and shaped to fit within the slot corresponding to the first lock portion when the device is in both the extended and locked configurations. In the depicted embodiment, the device may be locked in an extended configuration by rotating the first and second housings relative to one another to move the key into engagement with the slot when the device 301 is in the extended configuration. The device 301 may then be moved from the locked configuration to the unlocked configuration when the device 301 is in the extended configuration by rotating the second housing portion 313 in the opposite direction relative to the first housing portion 311 to move the second lock portion 323 out the first lock portion 321 and into alignment with the groove such that the key may move axially within the groove as the first and second housing portions are moved axially relative to one another.

As previously described, in some embodiments, such as those of FIG. 3, the device 301 also comprises a spring 309 that biases the housing portions 311 and 313 as well as the associated tissue grippers 302 and 303 towards a retracted configuration. The spring 309 is configured to operatively couple to the first housing portion 311 and the second housing portion 313 via any appropriate connection between the first housing portion 311 and the second housing portion 313 (corresponding hooks for engaging the loops 380 of the spring not shown). In some embodiments, the device may also include a force indicator as previously described. In this particular embodiment, the second lock portion 323 may function as the marker described above relative to FIGS. 2A and 2B. For example, the force indicator may include a plurality of markings 325 on the first housing portion 311. When released, the second lock portion 323, which is connected to the second housing portion 313, moves axially within the associated groove 342 relative to the plurality of markings as the device transitions between the extended and retracted configurations to indicate the retraction force.

Thus, in some embodiments, such as the embodiment illustrated in FIG. 3, a locking feature may also be used as a marker of a force indicator.

While particular types of lock and force indicator constructions are described above relative to FIGS. 2A-3, it should be understood that any appropriate type of lock and/or force indicator may be used as previously described. Additionally, the disclosed concepts may either be used in combination with each other or individually as the disclosure is not so limited.

Figure 4A:
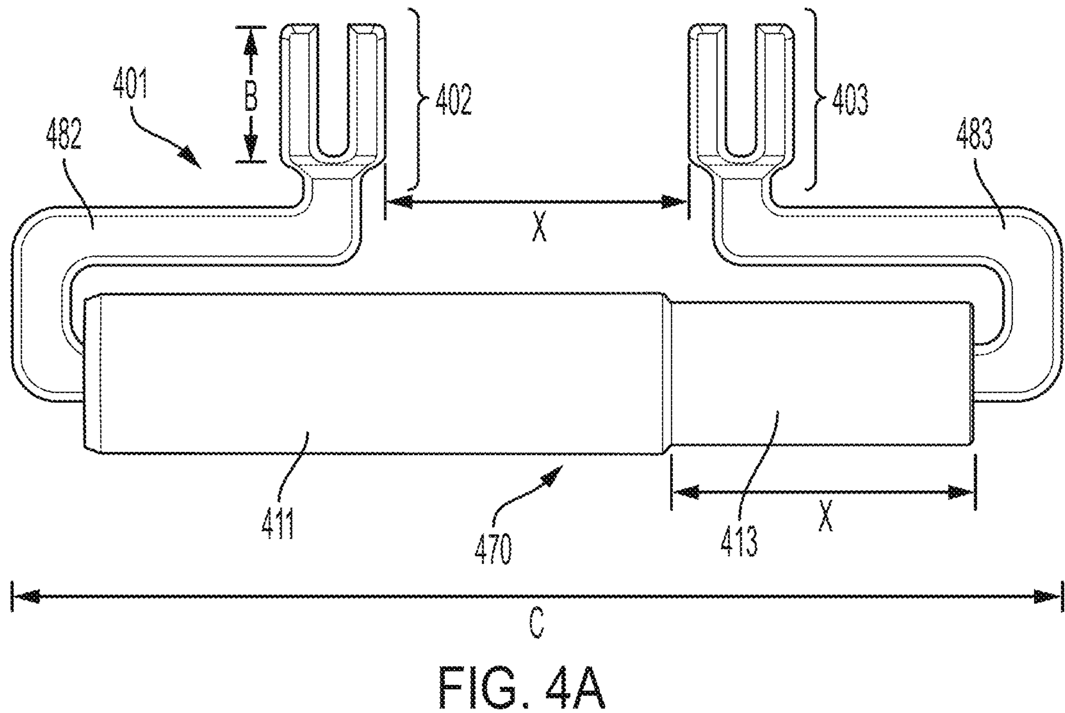
FIGS. 4A-4B present illustrations of a device for tissue closure, according to certain embodiments.
Figure 4B:
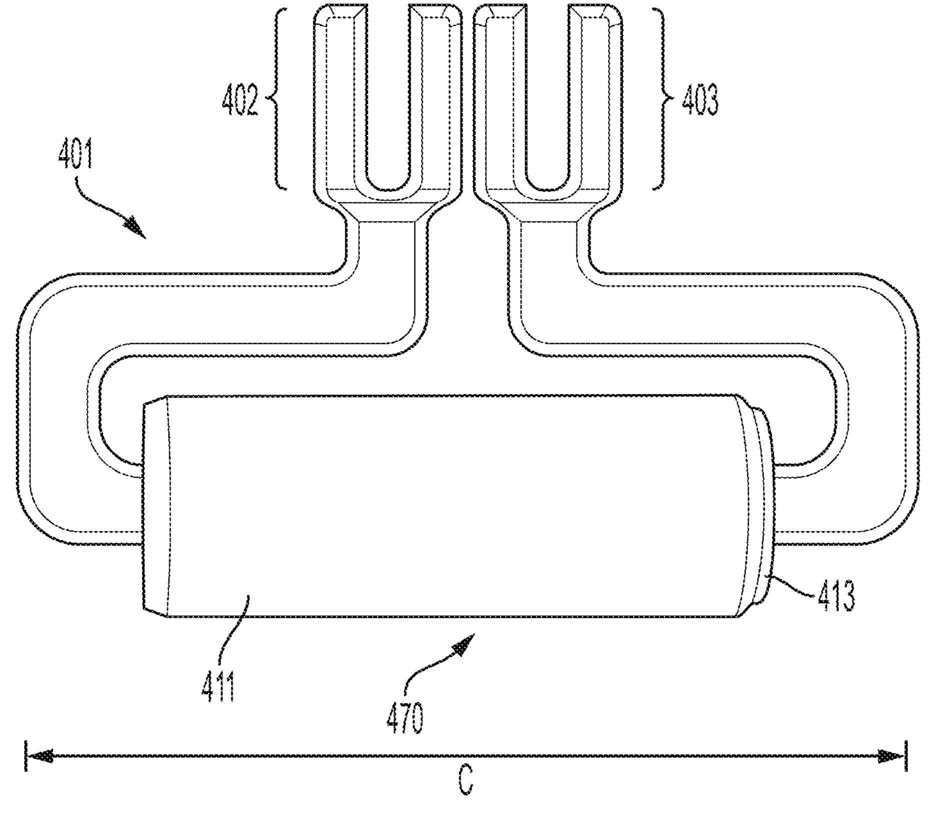

FIGS. 4A and 4B present another embodiment of a device for tissue closure. FIG. 4A presents a tissue closure device 401 in an extended configuration, according to certain embodiments. In some embodiments, such as those of FIGS. 1A-1C, FIGS. 2A-2B, and FIG. 3, the tissue grippers are oriented such that engaged tissue portions are pulled towards the spring when the device transitions from an extended configuration to a retracted configuration. In such embodiments, clamping forces may be symmetric, such that the retraction force is equal to the retention force of the tissue grippers. However, in some embodiments, such as the embodiment depicted in FIG. 4A, a first tissue gripper 402 and a tissue gripper 403 are oriented such that engaged tissue portions are not pulled towards a spring enclosed within a housing 470 of the device 401 when the device 401 transitions from an extended configuration to a retracted configuration. Rather, in some embodiments, the tissue portions engaged by the first tissue gripper 402 and the second tissue gripper 403 are pulled in a direction along an axis that is parallel to and offset from the housing 470 and a spring disposed therein when the device transitions from an extended configuration to a retracted configuration.

In some embodiments, such as the embodiment illustrated in FIG. 4A, the first tissue gripper 402 is connected to the first housing portion 411 via a first arm 482. In some embodiments, such as the embodiment illustrated in FIG. 4A, the second tissue gripper 403 is connected to the second housing portion 413 via a second arm 483. The first arm 482 and or the second arm 483 may be a rigid connection attached to any appropriate portion of the housing including, for example, an end portion of the housing 470. In the depicted embodiment the arm extends around the end portion of the housing 470 in order to extend parallel to and adjacent to the housing 470, before bending away from the housing 470 and connecting to an associate tissue gripper. According to certain embodiments, such a configuration may be advantageous, because it may permit a minimum distance X between the first tissue gripper 402 and the second tissue gripper 403 that is smaller than an axial length C of the housing in the retracted configuration. In some embodiments, this means that the minimum distance X between the first tissue gripper 402 and the second tissue gripper 403 can be as low as 0. In other words, the grippers may be disposed against one another in the fully retracted configuration in some embodiments. For example, FIG. 4B presents the device of FIG. 4A in a retracted configuration with the first tissue gripper and the second tissue gripper nearly touching.

In some embodiments, a tissue closure device comprises a cantilever lock. In some embodiments, such as embodiments of the type presented in FIG. 5A, a device comprises a first housing portion 511, comprising a first lock portion 521, which may be a catch such as the depicted hole, or any other structure configured to receive a key in the locked configuration. The device may further comprise a second housing portion 513, comprising a cantilever 540 connected to a second lock portion 523 (illustrated as a key, in the case of FIG. 5A) configured to be received by first lock portion 521.

Figure 5A:
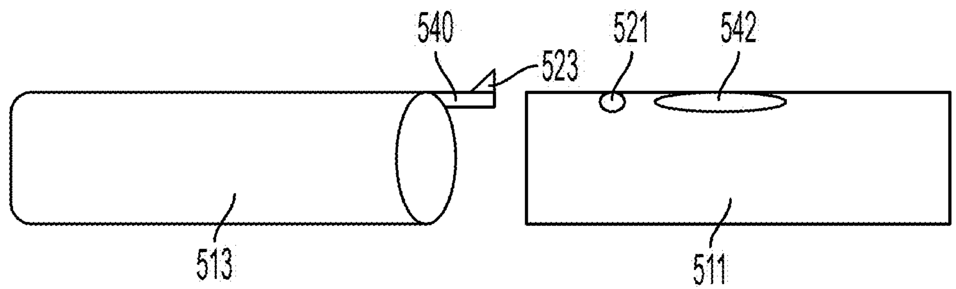
FIGS. 5A-5C present illustrations of a housing comprising a cantilever lock, according to certain embodiments.
Figure 5B:
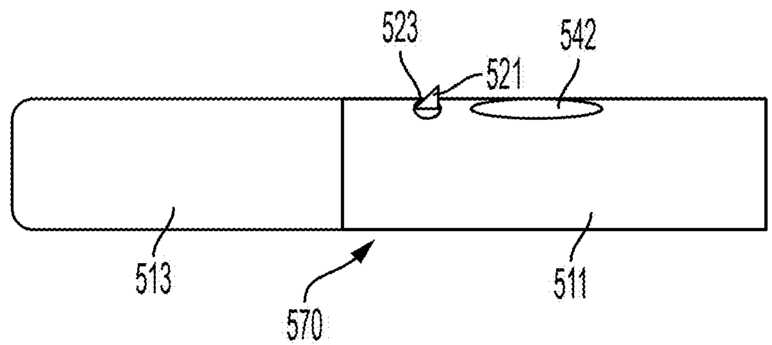
Figure 5C:
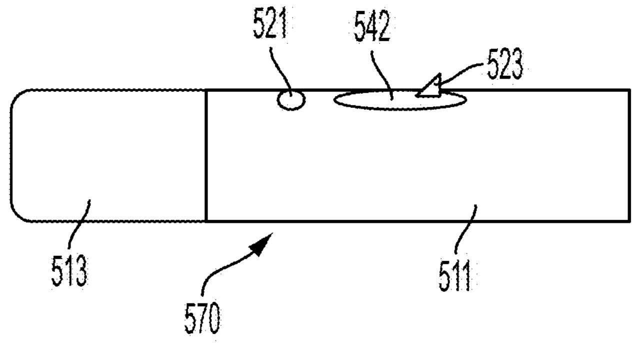

FIG. 5B illustrates the assembled housing portions of FIG. 5A in a locked configuration and in an extended configuration. Here, the second lock portion 523, a key connected to the cantilever 540, is engaged with the first lock portion 521 where the key is positioned in the hole formed in the other housing portion in order to lock first housing portion 511 in the extended configuration relative to second housing portion 513. In order to unlock the device, in some embodiments, a force may be applied to the second locking feature to depress the key out of engagement with the illustrated catch. Specifically, a force that is oriented radially inwards relative to the device is applied to the key to elastically deform the cantilever by a sufficient amount to decouple the first lock portion 521 from the second lock portion 523, allowing the first housing portion 511 to slide relative to the second housing portion 513. Optionally the first housing portion 511 may comprise a groove 542, recess, or other structure sized and shaped to permit the second lock portion, i.e. the depicted key, to be displaced in the axial direction after it is decoupled from the first lock portion. As illustrated in FIGS. 5A-5C, the use of a groove, or similar axially extending structure, may prevent rotation of the first housing portion 511 relative to the second hosing portion 513 in the unlocked configuration. However, the groove is not necessary in all embodiments, since in the unlocked configuration the first housing portion 511 can still slide relative to the second housing portion 513, even with the cantilever under stress such that it is pressed against an interior surface of the second housing portion.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A tissue closure device, comprising:

a first tissue gripper;

a second tissue gripper;

a spring operatively coupled to the first tissue gripper and the second tissue gripper;

a lock configured to retain the first tissue gripper and the second tissue gripper in an extended configuration in a locked configuration, wherein the spring is configured to bias the first tissue gripper and the second tissue gripper towards a retracted configuration when the lock is in an unlocked configuration; and a housing including a first housing portion and a second housing portion, wherein the first tissue gripper is operatively coupled to the first housing portion and the second tissue gripper is operatively coupled to the second housing portion, wherein at least a portion of the second housing portion is configured to slide into an interior volume of the first housing portion, and wherein the second tissue gripper is configured to move with the second housing portion in the same direction as the second housing portion.

2. The tissue closure device of claim 1, wherein the lock is selected from the group consisting of a cantilever lock and a slot and key lock.

3. The tissue closure device of claim 1, wherein a minimum distance between the first tissue gripper and the second tissue gripper in the retracted configuration is greater than or equal to 0 cm and less than or equal to 2 cm.

4. The tissue closure device of claim 1, wherein a maximum longitudinal dimension of the device is greater than or equal to 5 cm and less than or equal to 20 cm.

5. The tissue closure device of claim 1, wherein a maximum transverse dimension of the housing is greater than or equal to 3 mm and less than or equal to 8 mm.

6. The tissue closure device of claim 1, wherein a width of the first tissue gripper and the second tissue gripper is greater than or equal to 3 mm and less than or equal to 8 mm.

7. The tissue closure device of claim 1, wherein a length of the first tissue gripper and the second tissue gripper is greater than or equal to 1 cm and greater than or equal to 2 cm.

8. The tissue closure device of claim 1, wherein the spring is operatively coupled to the first housing portion and the second housing portion to bias the first housing portion towards the second housing portion.

9. The tissue closure device of claim 1, wherein, in the retracted configuration, the portion of the second housing portion disposed within the interior volume of the first housing portion is maximized.

10. The tissue closure device of claim 1, further comprising a force indicator configured to visually indicate a retraction force applied by the first and second tissue grippers to a first tissue portion and a second tissue portion.

11. The tissue closure device of claim 1, wherein the spring is at least one selected from the group of a coil spring, a rotary spring, a gas spring, a draw bar spring, and an elastic component.

12. The tissue closure device of claim 1, wherein the spring is configured to apply a retraction force greater than or equal to 2.5 N and less than or equal to 6 N.

13. The device of claim 1, wherein the first tissue gripper and the second tissue gripper have a closed configuration and an open configuration, and wherein the first tissue gripper and the second tissue gripper are biased towards the closed configuration.

14. The device of claim 1, wherein the first tissue gripper and the second tissue gripper are configured to apply force to a tissue portion atraumatically.

15. The device of claim 1, wherein the first tissue gripper and/or the second tissue gripper are configured to release if a retraction force is greater than a threshold retraction force.

16. The device of claim 1, wherein the second tissue gripper is directly connected to the second housing portion.

17. The tissue closure device of claim 1, wherein the lock includes a first lock portion coupled to the first housing portion and a second lock portion coupled to the second housing portion.

18. A method for closing an aperture in tissue, the method comprising:

retaining a first tissue gripper engaged with a first tissue portion and a second tissue gripper engaged with a second tissue portion in an extended configuration;

changing a lock from a locked configuration to an unlocked configuration to release the first tissue gripper and the second tissue gripper from the extended configuration;

biasing the first tissue gripper towards the second tissue gripper to move the first tissue gripper and the first tissue portion towards the second tissue gripper and the second tissue portion, wherein the first tissue gripper is operatively coupled to a first housing portion and the second tissue gripper is operatively coupled to a second housing portion; and sliding at least a portion of the second housing portion into an interior volume of the first housing portion when the first tissue gripper is biased towards the second tissue gripper, wherein the second tissue gripper is configured to move with the second housing portion in the same direction as the second housing portion.

19. The method of claim 18, further comprising visually indicating a retraction force applied by the first and second tissue grippers to the first and second tissue portions using a force indicator.

20. The method of claim 18, wherein the lock includes a first lock portion coupled to the first housing portion and a second lock portion coupled to the second housing portion.

21. A tissue closure device, comprising:

a first tissue gripper configured to apply a first clamping force to a first tissue portion;

a second tissue gripper configured to apply a second clamping force to a second tissue portion;

a spring operatively coupled to the first tissue gripper and the second tissue gripper;

a housing including a first housing portion and a second housing portion, wherein the first tissue gripper is operatively coupled to the first housing portion and the second gripper is operatively coupled to the second housing portion, wherein the spring is configured to bias the first tissue gripper and the second tissue gripper from an extended configuration towards a retracted configuration; and a force indicator configured to visually indicate a retraction force applied by the first and second tissue grippers to the first tissue portion and the second tissue portion, wherein at least a portion of the second housing portion is configured to slide into an interior volume of the first housing portion, and wherein the second tissue gripper is configured to move with the second housing portion in the same direction as the second housing portion.

22. The tissue closure device of claim 21, further comprising a lock configured to retain the first tissue gripper and the second tissue gripper in the extended configuration in a locked configuration.

23. The tissue closure device of claim 21, wherein the housing and the spring are coaxial.

24. The tissue closure device of claim 21, wherein the spring is at least partially disposed within an interior volume of the first housing portion and/or the second housing portion.

25. The tissue closure device of claim 21, wherein the force indicator includes a plurality of markings on an external surface of the first housing portion and/or the second housing portion and a marker configured to move relative to the plurality of markings as the device transitions between the extended and retracted configurations to indicate the retraction force.

26. A method for closing an aperture in tissue, the method comprising:

retaining a first tissue gripper engaged with a first tissue portion by a first clamping force and a second tissue gripper engaged with a second tissue portion by a second clamping force in an extended configuration;

biasing the first tissue gripper towards the second tissue gripper to move the first tissue gripper and the first tissue portion towards the second tissue gripper and the second tissue portion, wherein the first tissue gripper is operatively coupled to a first housing portion and the second tissue gripper is operatively coupled to a second housing portion;

visually indicating a retraction force applied by the first and second tissue grippers to the first and second tissue portions using a force indicator; and sliding at least a portion of the second housing portion into an interior volume of the first housing portion when the first tissue gripper is biased towards the second tissue gripper, wherein the second tissue gripper is configured to move with the second housing portion in the same direction as the second housing portion.

27. The method of claim 26, further comprising changing a lock from a locked configuration to an unlocked configuration to release the first tissue gripper and the second tissue gripper from the first, extended configuration.

* * * * *